(12) United States Patent
Ihara et al.

(10) Patent No.: US 6,710,074 B2
(45) Date of Patent: Mar. 23, 2004

(54) COMPOUND HAVING ANTIMALARIAL ACTIVITY

(75) Inventors: Masataka Ihara, Sendai (JP); Kiyosei Takasu, Sendai (JP); Yusuke Wataya, Okayama (JP); Hye-Sook Kim, Okayama (JP)

(73) Assignee: Japan Science and Technology Corporation, Kawaguchi (JP)

( * ) Notice: Subject to any disclaimer, the term of this patent is extended or adjusted under 35 U.S.C. 154(b) by 0 days.

(21) Appl. No.: 10/220,244

(22) PCT Filed: Mar. 1, 2001

(86) PCT No.: PCT/JP01/01568

§ 371 (c)(1),
(2), (4) Date: Aug. 30, 2002

(87) PCT Pub. No.: WO01/64682

PCT Pub. Date: Sep. 7, 2001

(65) Prior Publication Data

US 2003/0078291 A1 Apr. 24, 2003

(30) Foreign Application Priority Data

Mar. 3, 2000 (JP) ........................ 2000-058736

(51) Int. Cl.[7] ..................... A61K 31/35; A61K 31/335; C07D 321/12; C07D 323/06
(52) U.S. Cl. ..................... 514/450; 514/452; 549/349; 549/368
(58) Field of Search ............... 549/349, 368; 514/450, 452

(56) References Cited

U.S. PATENT DOCUMENTS

| 5,763,442 A | 6/1998 | Medlen et al. |
| 5,932,591 A | 8/1999 | Posner et al. |

FOREIGN PATENT DOCUMENTS

| JP | 5-97665 A | 4/1993 |
| JP | 6-157308 A | 6/1994 |
| JP | 7-82165 A | 3/1995 |
| JP | 8-59471 A | 3/1996 |
| JP | 8-73335 A | 3/1996 |
| JP | 8-231401 A | 9/1996 |
| JP | 10-265382 A | 10/1998 |
| JP | 11-228408 A | 8/1999 |
| JP | 11-228422 A | 8/1999 |
| JP | 11-228446 A | 8/1999 |
| JP | 2000-7673 A | 1/2000 |
| WO | WO 00/04025 A1 | 1/2000 |

OTHER PUBLICATIONS

Kathlyn A. Parker et al., "A Stereocontrolled Synthesis of dl–Biflora–4,10 (19), 15–triene[1]", J. Org. Chem., 1986, pp. 4023–4028, vol. 51, No. 21.

Primary Examiner—Alan L. Rotman
Assistant Examiner—Raymond Covington
(74) Attorney, Agent, or Firm—Venable LLP; Robert Kinberg

(57) ABSTRACT

An object of the present invention is to provide a novel compound having antimalarial acitivity and an antimalarial agent containing the novel compound as an active component. An antimalarial agent containing 12-hidroxy-2-(1-methoxy-carbonylethyl)-5-oxo-10,11,13-trioxatricyclo [7.2.0.0[1,6]]tridecane represented by a following formula (II) as an active agent is prepared.

(II)

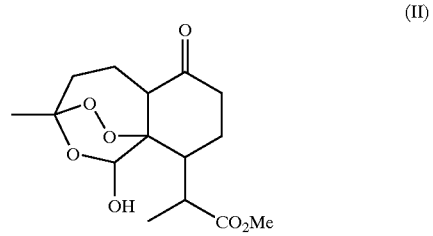

4 Claims, No Drawings

US 6,710,074 B2

COMPOUND HAVING ANTIMALARIAL ACTIVITY

TECHNICAL FIELD

The present invention relates to a novel compound having antimalarial activity and an antimalarial agent containing the novel compound as an active component.

BACKGROUND ART

Malaria is spread from person to person by the bite of a mosquito, Anopheles spp. A malaria parasite, being injected into a human body as a sporozoite together with saliva of a mosquito, enters into a hepatocyte and multiplies as an exoerythrocytic form (tissue form) parasite, and 10 to 14 days later, the parasite becomes a schizozoite and enters into the bloodstream to cause an infection, then multiplies through asexual reproduction wherein the parasite grows to a trophozoite, and to a schizont. A schizozoite, which corresponds to a seed of a plant, is produced in a mature schizont, and this schizozoite (merozoite) spills and enters into another erythrocyte, and then repeats its asexual reproduction. Although some of the schizozoites become male or female gametocytes without asexual reproduction, schizozoites cannot proliferate further in a human body, and schizozoites do not become male or female gametes and mate for sexual reproduction until they enter into the body of a mosquito. After several stages, such gamete matures and becomes a sporangium which has numerous sporozoites inside, and when a mosquito sucks the blood of human, such sporozoites are transfused into the human body together with saliva of the mosquito. There are four kinds of malaria parasites that infect human: *Plasmodium falciparum*, *Plasmodium vivax*, *Plasmodium ovale* and *Plasmodium malariae*, and it is estimated that 200 to 300 million people are infected with malaria in the world, and that two to three million people die from malaria every year. In recent years, there emerge insecticide-resistant mosquitoes and chloroquine-resistant malaria parasites, and it is becoming difficult to deal with these organisms.

As an antimalarial agent or an antimalarial compound, the following are conventionally known: a novel compound of ortho-condensation system containing two heterocycles as described in Japanese Laid-Open Patent Application No. 2000-7673; an antimalarial agent containing a compound having ICAM-1 expression suppressing activity as an active component as described in Japanese Laid-Open Patent Application No. 11-228446; an antimalarial agent containing a nucleoside derivative and the like such as 5'-o-sulfamoyl-2-chloroadenosine or the like as an active component as described in Japanese Laid-Open Patent Application No. 11-228422; an antimalarial agent containing tricothecenes and the like as an active component as described in Japanese Laid-Open Patent Application No. 11-228408; an antimalarial agent containing cycloprodigiosin and the like as an active component as described in Japanese Laid-Open Patent Application No. 10-265382; a drug for preventing or treating malaria containing riminophenazine as an active component as described in Japanese Laid-Open Patent Application No. 8-231401; an agent for overcoming antimalarial drug resistance containing a quinoline derivative and the like as an active component as described in Japanese Laid-Open Patent Application No. 8-73355; an antimalarial agent containing 5-fluoroorotic acid and sulfamonomethoxyne as an active component as described in Japanese Laid-Open Patent Application No. 8-59471; an antimalarial agent containing *Astragalus membranaceus*, *Cinnamomum cassia*, *Rehmanniae Radix*, *Paeonia lactiflora*, *Cnidii Rhizoma*, *Atractylodis Lanceae Rhizoma*, *Angelicae Radix*, *Panax ginseng*, *Poria cocos* and *Glycyrrhizae Radix*, or extracts thereof as an active component as described in Japanese Laid-Open Patent Application No. 7-82165; an antimalarial agent containing a tetrapyrrole derivative and the like as an active component as described in Japanese Laid-Open Patent Application No. 6-157308; an antimalarial agent containing 15-deoxyspergualin and the like as an active component as described in Japanese Laid-Open Patent Application No. 5-97665.

Malaria is a serious infection. 200 to 300 million people are infected with malaria and two to three million people die from malaria every year. Further, the emergence of a malaria parasite resistant to chloroquine, which is a drug heavily used as a panacea of malaria, has become a serious problem, and therefore, there is an urgent need to develop an effective remedy. Artemisinin, which is isolated from plants that belong to Asteraceae and has a trioxa structure, is effective to chloroquine-resistant malaria parasites, and this nature derived compound is currently used as a remedy. However, a malaria parasite which shows resistance also to artemisinin has already emerged as well, and it is causing a more serious problem. An object of the present invention is to provide a novel compound having antimalarial activity and an antimalarial agent containing the novel compound as an active component.

DISCLOSURE OF THE INVENTION

The inventors of the present invention have conducted intensive study as to synthesis of artemisinin analogues in order to attain the above-mentioned object, and found that 12-hidroxy-2-(1-methoxycarbonylethyl)-5-oxo-10,11,13-trioxatricyclo[7.2.0.0$^{1,6}$]tridecane synthesized by utilizing photooxidation reaction, from bicyclic olefin synthesized by intramolecular Diels-Alder reaction, shows extremely high antimalarial activity and selective toxicity, and the present invention has been thus completed.

The present invention relates to a compound represented by a following general formula (I) [wherein $R^1$ represents a hydrogen atom or an optionally branched C1–C6 alkyl group, $R^2$ represents a hydrogen atom, an optionally branched C1–C6 alkyl group or an optionally substituted aryl group, $R^3$ represents an oxygen atom, a sulfur atom, $NR^4$ ($R^4$ represents a hydrogen atom or an optionally branched C1–C6 alkyl group) or $CR^5_2$ ($R^5$ each independently represents a hydrogen atom or an optionally branched C1–C6 alkyl group)](claim 1), Chemical Formula 1

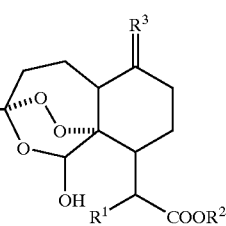

(I)

and the compound according to claim 1, wherein the compound represented by the general formula (1) is 12-hidroxy-2-(1-methoxycarbonylethyl)-5-oxo-10,11,13-trioxatricyclo[7.2.0.0$^{1,6}$]tridecane represented by a following formula (II) (claim 2).

Chemical Formula 2

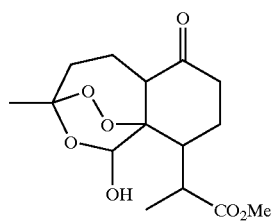

(II)

The present invention further relates to an antimalarial agent containing a compound represented by a following general formula (I) [wherein $R^1$ represents a hydrogen atom or an optionally branched C1–C6 alkyl group, $R^2$ represents a hydrogen atom, an optionally branched C1–C6 alkyl group or an optionally substituted aryl group, $R^3$ represents an oxygen atom, a sulfur atom, $NR^4$ ($R^4$ represents a hydrogen atom or an optionally branched C1–C6 alkyl group) or $CR^5_2$ ($R^5$ each independently represents a hydrogen atom or an optionally branched C1–C6 alkyl group)] as an active component (claim 3), Chemical Formula 3

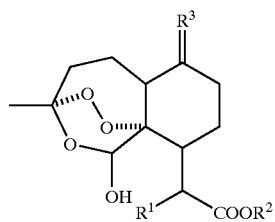

(I)

and the antimalarial agent according to claim 3, wherein the compound represented by the general formula (I) is 12-hidroxy-2-(1-methoxycarbonylethyl)-5-oxo-10,11,13-trioxatricyclo[7.2.0.0$^{1,6}$]tridecane represented by a following formula (II) (claim 4).

Chemical Formula 4

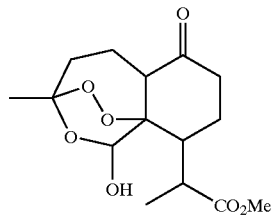

(II)

BEST MODE TO CARRY OUT THE INVENTION

In the compound represented by the general formula (I) according to the present invention, $R^1$ represents a hydrogen atom or an optionally branched C1–C6 alkyl group, and specific examples of such optionally branched C1–C6 alkyl group include a methyl group, an ethyl group, an isopropyl group and a t-butyl group. $R^2$ represents a hydrogen atom, an optionally branched C1–C6 alkyl group or an optionally substituted aryl group, and specific examples of such optionally branched C1–C6 alkyl group include a methyl group, an ethyl group, an isopropyl group and a t-butyl group, and those of the optionally substituted aryl group include a phenyl group, a tolyl group and a naphthyl group, respectively. In addition, as a substituent in the aryl group, an optionally branched C1–C6 alkyl group, an optionally branched C1–C6 alkoxy group and the like are exemplified.

Further, in the compound represented by the general formula (I) according to the present invention, $R^3$ represents an oxygen atom, a sulfur atom, $NR^4$ ($R^4$ represents a hydrogen atom or an optionally branched C1–C6 alkyl group) or $CR^5_2$ ($R^5$ each independently represents a hydrogen atom or an optionally branched C1–C6 alkyl group). As $R^4$ in $NR^4$, a hydrogen atom, a methyl group, an ethyl group, an isopropyl group, a t-butyl group and the like are specifically exemplified. Specific examples of $R^5$ in $CR^5_2$ include a hydrogen atom, a methyl group, an ethyl group, an isopropyl group and a t-butyl group. These two $R_5$ may be same or different.

Among these compounds represented by the general formula (I), 12-hidroxy-2-(1-methoxycarbonylethyl)-5-oxo-10,11,13-trioxatricyclo[7.2.0.0$^{1,6}$]tridecane represented by the formula (II) having excellent antimalarial activity is preferable in view of antimalarial activity and selective toxicity.

A method of producing the compound represented by the general formula (I) according to the present invention and 12-hidroxy-2-(1-methoxycarbonylethyl)-5-oxo-10,11,13-trioxatricyclo[7.2.0.0$^{1,6}$]tridecane represented by the formula (II) is not particularly limited. For example, said compounds can be obtained as a peroxide moiety by a method comprising the steps of: triene is synthesized from 1,4-butanediol derivative by several steps of known synthetic reaction; the synthesized triene is stereoselectively transformed into cis-decalone through Dess-Martin oxidation followed by intramolecular Diels-Alder reaction; the cis-decalone is subjected to base treatment and then to singlet oxygen oxidation-air oxidation (Roth's method).

When the compound according to the present invention is used for prevention, inhibition and treatment of infection caused by malaria parasites, any of oral administration, subcutaneous injection, intravenous injection, local administration or the like can be used as an administration route. As examples of drugs, drugs for oral administration such as powders, tablets, subtle granules, pills, capsules, granules or the like and those for parenteral administration such as instillations, injectable solutions, suppositories or the like, both formulated by using pharmaceutically acceptable carriers, excipients and other additives, are usually exemplified. Examples of pharmaceutically acceptable carriers, excipients and other additives include glucose, lactose, gelatin, mannitol, starch paste, magnesium trisilicate, corn starch, keratin, coloidal silica, and it may further contain adjuvants such as a stabilizer, an expander, a colorant and an aromatic substance. Each of these drugs can be produced by methods conventionally known to person skilled in the art. In addition, though the dose per day depends on symptom, weight, age, sex and the like of patients and cannot be determined uniformly, it is usually preferable to administer 0.1 to 1000 mg, more preferably 1 to 600 mg, of the compound according to the present invention per day to adult patients.

The present invention is explained below with reference to examples, but the technical scope of the present invention is not limited to these examples. Example 1 [Production of 12-hidroxy-2-(1-methoxycarbonyl-ethyl)-5-oxo-10,11,13-trioxatricyclo[7.2.0.0$^{1,6}$]tridecane] 12-hidroxy-2-(1-methoxycarbonylethyl)-5-oxo-10,11,13-trioxatricyclo[7.2.0.0$^{1,6}$]tridecane was synthesized by using (4E)-7- methyl-1-tetrahydropyranoxy-4,7-octadien-6-ol as a starting material. The starting material represented by a following formula (1), (4E)-7-methyl-1-tetrahydropyranoxy-4,7-octadien-6-ol was synthesized according to the method as previously described (the Journal of Organic Chemistry, Vol. 51, 4023-4028, 1986).

Chemical Formula 5

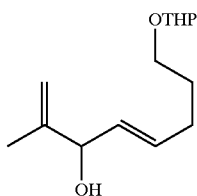

(1)

EXAMPLE 1-1

Synthesis of a Novel Substance, (4E)-7-methyl-6-propanoyloxy-1-tetrahydropyranoxy-4,7-octadien-6-ol 7.26 g of (4E)-7-methyl-1-tetrahydropyranoxy-4,7-octadien-6-ol (1) and 7.4 ml of pyridine were put in methylene chloride solution (65 ml). 3.1 ml of propionyl chloride was added dropwise to the solution at 0° C., and the resulting mixture was stirred for 30 minutes. Subsequently, the mixture was added with water and subjected to diethyl ether extraction, and its organic layer was washed with 10% of aqueous potassium hydrogen sulfate and saturated saline, then dried over anhydrous magnesium sulfate. Residues obtained by refluxing a solvent under reduced pressure were subjected to silica gel column chromatography, and 7.74 g of achromatic oily substance was obtained at 86% yield from a hexan-ethyl acetate (10:1 v/v) eluting section. Physical property of the obtained substance is as follows, and a structural formula of a compound based on the physical property is shown in a formula (2).

IR (neat) cm$^{-1}$: 1740. $^1$H-NMR (300 MHz, CDCl$_3$) δ: 1.15 (3H, t, J=7.5 Hz), 1.47–1.76 (8H, m), 1.72 (3H, s), 2.10–2.20 (2H, m), 2.36 (2H, q, J=7.5 Hz), 3.32–3.54 (4H, m), 3.68–3.90 (4H, m), 4.53–4.60 (1H, m), 4.88 (1H, s), 4.98 (1H, s), 5.45 (1H, dd, J=14.5, 7.0 Hz), 5.57 (1H, d, J=7.0 Hz), 5.75 (1H, dd, J=14.5, 7.0 Hz). MS m/z: 295 (M+-1). Elemental analysis Calcd for C$_{17}$H$_{28}$O$_4$: C, 68.87; H, 9.52. Found: C, 69.02; H, 9.39.

Chemical Formula 6

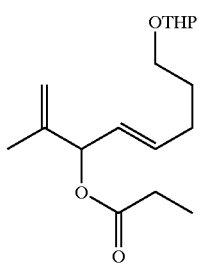

(2)

EXAMPLE 1-2

Synthesis of a Novel Substance, methyl(2S*, 3R*, 4E)-2,6-dimethyl-3-[3'-(tetrahydropyranoxy)propyl]-hepta-4,6-dienoate 5.1 ml of butylithium in hexan solution (1.54 M) was added dropwise to THF solution (50 ml) containing 1.51 ml of diisopropylamine at 0° C., and then the resulting solution was stirred for 30 minutes at 0° C. and for 1 hour at −78° C. 1.0 g of the obtained compound (2) above in tetrahydrofuran solution (5 ml) was added dropwise to the above solution in 1 hour and then the resulting mixture was stirred for 1 hour at −78° C. After that, the mixture was added with 1.03 ml of chlorotrimethylsilane and stirred for 1 hour, and gradually warmed to room temperature and stirred for 2 hours. After the reaction was completed, the mixture was added with 2 ml of methanol and stirred for 30 minutes. Residues obtained by refluxing a solvent were basified by aqueous sodium bicarbonate and subjected to back extraction. The obtained water layer was acidified by 10% of potassium hydrogen sulfate, followed by extraction with ethyl acetate. Its organic layer was washed with saturated saline, then dried over anhydrous magnesium sulfate. Residues obtained by refluxing a solvent under reduced pressure were added with ether (3 ml), then added dropwise with an excessive amount of diazomethane in diethyl ether solution at 0° C., and the resulting mixture was stirred for 1 hour. Residues obtained by refluxing a solvent under reduced pressure were subjected to silica gel column chromatography, and 0.76 g of light yellow oily substance was obtained at 72% yield from a hexan-ethyl acetate (9:1 v/v) eluting section. Physical property of the obtained substance is as follows, and a structural formula of a compound based on the physical property is shown in a formula (3).

IR (neat) cm$^{-1}$: 1725. $^1$H-NMR (300 MHz, CDCl$_3$) δ: 1.04 (3H, d, J=6.6 Hz), 1.18–1.80 (9H, m), 1.79 (3H, s), 2.31–2.47 (2H, m), 3.27–3.39 (2H, m), 3.41–3.55 (2H, m), 3.64 (3H, s), 3.77–3.87 (2H, m), 4.54 (1H, br s), 4.86 (2H, br s), 5.28 (1H, dd, J=15.7, 9.3 Hz), 6.11 (1H, d, J=15.7 Hz). MS m/z: 310 (M+). Elemental analysis Calcd for C$_{18}$H$_{30}$O$_4$: C, 69.64; H, 9.74. Found: C, 69.87; H, 10.04.

Chemical Formula 7

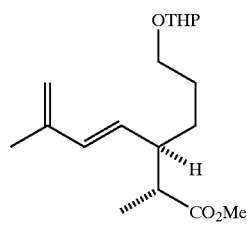

(3)

EXAMPLE 1-3

Synthesis of a Novel Substance, methyl(2S*, 3R*, 4E)-3-(3'-hydroxypropyl)-2,6-dimethylhepta-4,6-dienoate 0.11 g of the obtained compound (3) above in methanol solution (6 ml) was added with 34 mg of toluenesulfonic acid•monohydrate at room temperature, and the resulting solution was stirred for 1 hour. Subsequently, residues obtained by refluxing a solvent under reduced pressure were added with saturated aqueous sodium bicarbonate, followed by extraction with ethyl acetate. The obtained organic layer was washed with saturated saline, then dried over anhydrous magnesium sulfate. Residues obtained by refluxing a solvent under reduced pressure were subjected to silica gel column chromatography, and 75.0 mg of achromatic oily substance was obtained at 94% yield from a hexan-ethyl acetate (2:1 v/v) eluting section. Physical property of the obtained substance is as follows, and a structural formula of a compound based on the physical property is shown in a formula (4).

IR (neat) cm$^{-1}$: 3400, 1740, 1610. $^1$H-NMR (300 MHz, CDCl$_3$) δ: 1.08 (3H, d, J=6.7 Hz), 1.30–1.83 (4H, m), 1.83 (3H, s), 2.24–2.45 (2H, m), 3.59–3.70 (2H, m), 3.68 (3H, s), 4.89 (2H, s), 5.27 (1H, dd, J=15.7, 9.3 Hz), 6.10 (1H, dd, J=15.7 Hz). MS m/z: 226 (M$^+$). Elemental analysis Calcd for C$_{13}$H$_{22}$O$_3$: C, 71.39; H, 9.59. Found: C, 71.12; H, 9.75.

Chemical Formula 8

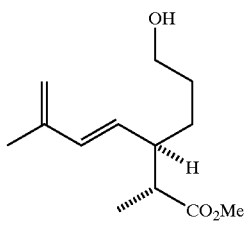

(4)

EXAMPLE 1-4

Synthesis of a Novel Substance, methyl(2S*, 3R*, 4E)-3-(3'-hydroxy-4-pentenyl)-2,6-dimethylhepta-4,6-dienoate 253 mg of the obtained compound (4) above in methylene chloride solution (4 ml) was sequentially added with 631 mg of pyridinium bichromate and 0.7 g of powdery 4 Å of molecular sieve at room temperature, and the resulting mixture was stirred for 1.5 hour. The mixture was diluted with diethyl ether and added with 1 g of Frolisil, then stirred for 10 minutes, followed by celite filtration. By refluxing a filtrate under reduced pressure, crude aldehyde was obtained as a yellow oily substance. This crude substance was put in tetrahydrofuran solution (3 ml), and added dropwise with 1.1 ml of vinyl magnesium bromide-tetrahydrofuran solution (1.0 M) at −78° C., and then the resulting solution was stirred for 20 minutes. Subsequently, saturated aqueous ammonium chloride was added to the solution at 0° C., then diethyl ether extraction was conducted. Its organic layer was washed with saturated saline, then dried over anhydrous magnesium sulfate. Residues obtained by refluxing a solvent under reduced pressure were subjected to silica gel column chromatography, and 0.18 g of achromatic oily substance was obtained at 65% yield from a hexan-ethyl acetate (4:1 v/v) eluting section. Physical property of the obtained substance is as follows, and a structural formula of a compound based on the physical property is shown in a formula (5).

IR (neat) cm$^{-1}$: 3500, 1740, 1620. $^1$H-NMR (300 MHz, CDCl$_3$) δ: 1.08 (3H, d, J=6.9 Hz), 1.25–1.69 (4H, m), 1.82 (3H, s), 2.23–2.45 (2H, m), 3.67 (3H, s), 4.08 (1H, br s), 4.90 (2H, s), 5.10 (1H, d, J=9.8 Hz), 5.21 (1H, d, J=16.5 Hz) 5.29 (1H, dd, J=9.0, 14.7 Hz), 5.76–5.90 (1H, m), 6.14 (1H, d, J=14.7 Hz). MS m/z: 295 (M$^+$−1). Elemental analysis Calcd for C$_{15}$H$_{24}$O$_3$: C, 68.99; H, 9.80. Found: C, 68.92; H, 9.88.

Chemical Formula 9

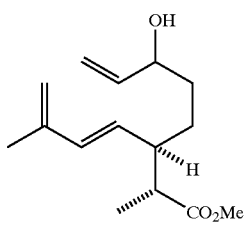

(5)

EXAMPLE 1-5

Synthesis of a Novel Substance, (1R*, 2R*, 6R*, 1'S*)-2-(1'-methoxycarbonylmethyl)-9-methylbicyclo[4.4.0] decane-9-ene-5-one The obtained compound (5) above (12.1 mg) in methylene chloride solution (0.5 ml) was added to Dess-Martin reagent (32.8 mg) in methylene chloride solution (1.0 ml) at 0° C., and then the resulting mixture was stirred for 2 hours at room temperature. Then, the mixture was poured into saturated aqueous sodium bicarbonate-2% of aqueous sodium thiosulfate (1:7 v/v), followed by diethyl ether extraction. Its organic layer was washed with water and saturated saline, then dried over anhydrous magnesium sulfate. Residues obtained by refluxing a solvent under reduced pressure were subjected to silica gel column chromatography, and 9.4 mg of light yellow oily substance was obtained at 78% yield from a hexan-ethyl acetate (6:1 v/v) eluting section. Physical property of the obtained substance is as follows, and a structural formula of a compound based on the physical property is shown in a formula (6).

IR (neat) cm$^{-1}$: 1720, 1705. $^1$H-NMR (500 MHz, CDCl$_3$) δ: 1.22 (3H, d, J=7.0 Hz), 1.47–1.56 (2H, m), 1.62 (3H, s), 1.85–1.94 (2H, m), 2.01–2.13 (2H, m), 2.24–2.45 (3H, m), 2.56 (1H, br s), 2.85 (1H, dt, J=7.0,7.0 Hz), 3.64–3.75 (3H, m), 5.32 [1H, br s]. MS m/z: 250 (M$^+$). HRMS m/z (M$^+$): Calcd for C$_{15}$H$_{22}$O$_3$: 250.1568. Found: 250.1530.

Chemical Formula 10

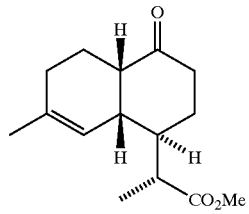

(6)

EXAMPLE 1-6

Synthesis of a Novel Substance, (1R*, 2R*, 6S*)-2-(1'-methoxycarbonylmethyl)-9-methylbicyclo[4.4.0] decane-9-ene-5-one 91 mg of the obtained compound (6) above in tetrahydrofuran solution (3 ml) was added with 73 mg of sodium hydride (60% of mineral oil suspension) at 0° C., and the mixture was stirred for 3 hours at room temperature. Subsequently, water was added to the mixture and diethyl ether extraction was conducted. The obtained organic layer was washed with saturated saline, then dried over anhydrous magnesium sulfate. Residues obtained by refluxing a solvent under reduced pressure were subjected to silica gel chromatography, and 90 mg of a mixture of said compound represented by the formula (6) and a compound represented by a formula (7) mentioned below was obtained as achromatic oily substance [compound (6):compound (7)=1:1.2] from a hexan-ethyl acetate (5:1 v/v) eluting section. Production was then stopped, and the product was used for next reaction.

Chemical Formula 11

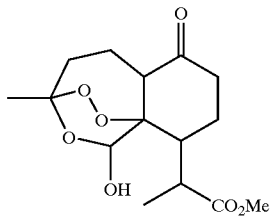

(7)

EXAMPLE 1-7

Synthesis of a Novel Substance of the Present Invention, 12-hidroxy-2-(1-methoxycarbonylethyl)-5-oxo-10,11,13-trioxatricyclo[7.2.0.0$^{1,6}$]tridecane Solution wherein 30 mg of the obtained mixture [of compound (6) and compound (7)] above was put in acetone solution (20 ml) was added with 0.9 mg of methylene blue, then irradiated by light of 100 W tungsten lamp for 24 hours at room temperature in oxygen airstream. After that, a solvent was refluxed under reduced pressure, and methylene blue was removed by filtration after diethyl ether was added to, and the filtrate was refluxed under reduced pressure. The obtained light yellow oily substance was suspended in petroleum ether (6 ml), and trifluoroacetic acid (0.01 ml) was added to the suspension, and the suspension was left for 24 hours at room temperature in air atmosphere. Subsequently, the petroleum ether dissolution was refluxed under reduced pressure, and the obtained residues were subjected to silica gel chromatography, and 1.8 mg of achromatic oily substance was obtained at 5% yield from a hexan-ethyl acetate (6:1 v/v) eluting section. Physical property of the obtained substance is as follows, and a structural formula of a compound based on the physical property was the one shown in the formula (II).

IR (neat) cm$^{-1}$: 1710, 1730. $^1$H-NMR (500 MHz, CDCl$_3$) δ: 1.20 (3H, d, J=7.0 Hz), 1.22–1.84 (4H, m), 1.86–1.89 (1H, m), 1.91 (3H, s), 2.05–2.20 (2H, m), 2.27–2.38 (2H, m), 2.54–2.61 (2H, m), 2.78 (1H, dd), 3.68–3.71 (1H, s), 3.69 (3H, s), 5.80 (1H, s). MS m/z: 314 (M$^+$).

EXAMPLE 2

Measurement of Antimalarial Activity and Selective Toxicity

Antimalarial activity and selective toxicity of the compound according to the present invention, 12-hidroxy-2-(1-methoxycarbonylethyl)-5-oxo-10,11,13-trioxatricyclo[7.2.0.0$^{1,6}$]tridecane, represented by the formula (II) as obtained in Example 1 was measured. Antimalarial activity was evaluated by measuring 50% inhibitory concentration, and selective toxicity was evaluated by calculating chemotherapeutic coefficient (selective toxicity).

EXAMPLE 2-1

Culture of *Plasmodium Falciparum*

*P. Falciparum* FCR-3 strain (ATCC30932) and *P. Falciparum* Honduras-i strain (ATCC30935), both of which are *Plasmodium falciparum*, were used as test malaria parasites for measuring antimalarial activity. A filter-sterilized RPMI1640 medium was adjusted to be pH 7.4 and added with human serum such that the serum made up 10% of the medium, and used as a test medium. The above-mentioned *P. falciparum* were cultured in O$_2$ at a concentration of 5%, CO$_2$ at a concentration of 5% and N$_2$ at a concentration of 90%, at a temperature of 36.5° C. Hematocrit value (ratio of volume of erythrocytes in erythrocyte suspension) used was adjusted to be 5%. Initial infection rate of *P. falciparum* at the beginning of culture was adjusted to be 0.1%. A 24-well plate was used for culture and a medium was replaced everyday, and cultures were transferred at infection rate of 4%. A thin-layer smear was constructed and subjected to Giemsa staining which had been originally developed for malarial test, or Diff-Qick staining, and followed by measurement under a microscope (oil immersion, 1000×), and then infection rate of *P. falciparum* was calculated according to a formula mentioned below.

Mathematical formula 1

$$\text{Infection rate of malarial parasite (\%)} = \frac{\text{number of infected erythrocytes}}{\text{total number of erythrocytes}} \times 100$$

EXAMPLE 2-2

Growth Inhibition Test of *P. Falciparum*

Cultured erythrocytes infected with *P. falciparum* were gathered by centrifugation and washed with a medium containing serum, then noninfected erythrocytes were added, and a culture liquid for *P. falciparum* at initial infection rate of 0.3% was prepared. Hematocrit value in this case was adjusted to be 3%. The compound according to the present invention used for a test and represented by the formula (II) and three kinds of positive control drug (quinine, artemisinin, artesunate, mefloquine) were dissolved into sterilized water, N,N-dimethylformamide (DMF) or dimethylsulfoxide (DMSO), and a sample solution at prescribed concentration was prepared. 5 to 10 μl of the sample solution was added to each well of a 24-well plate. The sample solution was duplicated or triplicated. For control, sterilized water, DMF or DMSO was added by 10 μl per well. Next, the above-mentioned culture liquid for *P. falciparum* prepared to be at initial infection rate of 0.3% was added by 990 to 995 μl each, and uniformly suspended in media by pipetting gently. After cultured for 72 hours in a CO$_2$—O$_2$—N$_2$ (5%, 5%, 90%) incubator, a thin-layer smear was constructed for each well of the culture plate, Giemsa staining or Diff-Qick staining was conducted, followed by measurement under a microscope (oil immersion, 1000×), and then infection rates of *P. falciparum* in a group supplemented with a test liquid and in controls were calculated. The growth inhibition rate was calculated according to a formula mentioned below based on the infection rate of *P. falciparum* as calculated above, and 50% growth inhibitory concentration (EC$_{50}$) was calculated.

$$\text{Growth inhibition rate (\%)} = \frac{1 - (b - a)}{(c - a)} \times 100 \quad \text{Mathematical formula 2}$$

a: initial infection rate
b: infection rate of a sample solution after 72 hours
c: infection rate of a control after 72 hours

EXAMPLE 2-3

Growth Inhibition Test of Mouse FM3A Cells

An F28-7 strain, a wild-type strain of mouse breast cancer-derived FM3A cells was used. Immobilized fetal bovine serum was added to an ES medium such that the serum made up 2% of the medium, and culture was conducted in $CO_2$ at a concentration of 5%, and at 37° C. Doubling time of the F28-7 strain of FM3A cells under this condition was about 12 hours. Cells which had been pre-cultured and entered to logarithmic growth phase were diluted to be $5 \times 10^4$ cells/ml in the medium. The same sample solution as in the above-mentioned Example 2-2 was used. 5 to 10 µl of the sample solution was added to each well of a 24-well plate (when medium and the like were added, the final concentration became $1 \times 10^{-4} \sim 1 \times 10^{-5}$ M). The sample solution was duplicated or triplicated, and wells added with 10 µl of sterilized water, DMF or DMSO were prepared at the same time as controls. Next, a prepared suspension of cultured cells was added by 990 to 995 µl each, and uniformly suspended in media by pipetting gently. After cultured for 48 hours, the number of cells in each well was counted by a cell counter (CC-108; Toa. Medical Electrics), and growth rate was calculated by a formula mentioned below and 50% growth inhibitory rate ($IC_{50}$) was calculated. The cell proliferation inhibiting activity was calculated according to the number of cells in wells supplemented with the sample solution and in controls. $Ba_{25}$ on this, cell toxicity of the sample was evaluated.

$$\text{Growth rate } (\%) = \frac{(C-A)}{(B-A)} \times 100 \qquad \text{Mathematical formula 3}$$

A: the number of cells at the beginning
B: the number of cells in a control after 2 days
C: the number of cells 2 days after supplementation of a sample

EXAMPLE 2-4

Assessment of Drug Efficacy

Antimalarial activity of a sample was evaluated based on $EC_{50}$ and $IC_{50}$ values of the sample of *P. falciparum* and mouse FM3A cells. Chemotherapeutic coefficient used as an index of selective toxicity against P falciparum was calculated by a formula mentioned below and drug efficacy was assessed.

$$\text{Chemotherapeutic coefficient} = \frac{IC_{50} \text{ value of the sample of mouse FM3A cells}}{EC_{50} \text{ value of the sample of } P.\ falciparum} \qquad \text{Mathematical formula 4}$$

With regard to the compound according to the present invention and positive control drugs, $EC_{50}$ and $IC_{50}$ values and chemotherapeutic coefficients of samples of *P. falciparum* and mouse FM3A cells are shown in Table 1. Judging from the results shown in Table 1, the compound according to the present invention is revealed to have low toxicity and extremely excellent growth inhibition activity against malaria parasites.

TABLE 1

| Compound | 50% growth inhibitory concentration (M) | | Chemotherapeutic coefficient |
|---|---|---|---|
| | $EC_{50}$ | $IC_{50}$ | $IC_{50}/EC_{50}$ |
| Compound of the present invention | $3.9 \times 10^{-8}$ | $2.4 \times 10^{-5}$ (78% growth) | >1,000 |
| Quinine | $1.1 \times 10^{-7}$ | $1.0 \times 10^{-4}$ | 910 |
| Artemisinin | $7.9 \times 10^{-9}$ | $1.0 \times 10^{-5}$ | 1,300 |
| Artesunate | $1.7 \times 10^{-8}$ | $3.0 \times 10^{-6}$ | 180 |
| Mefloquine | $3.2 \times 10^{-8}$ | $2.9 \times 10^{-6}$ | 90 |

INDUSTRIAL APPLICABILITY

The novel compound having antimalarial activity according to the present invention inhibits the growth of drug-resistant *P. falciparum* at a mol concentration of $3.9 \times 10^{-8}$, and its selective toxicity against *P. falciparum* is more than 1,000 times as strong as that against mouse FA3A cells, and therefore, is extremely useful as an antimalarial agent.

What is claimed:

1. A compound represented by a following general formula (I);

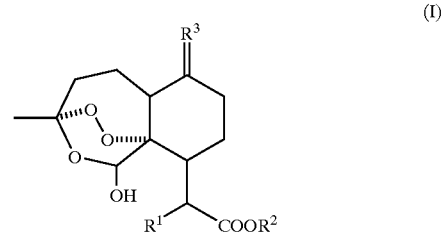

(I)

2. The compound according to claim 1, wherein the compound represented by the general formula (I) is 12-hidroxy-2-(1-methoxycarbonylethyl)-5-oxo-10,11,13-trioxatricyclo [$7.2.0.0^{1,6}$]tridecane represented by a following formula (II).

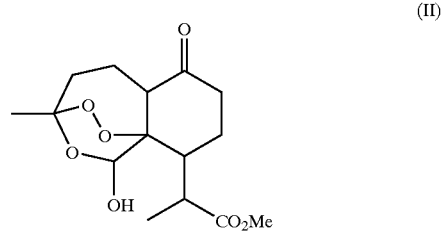

(II)

3. A therapeutic agent for malaria containing a compound represented by a following general formula (I);

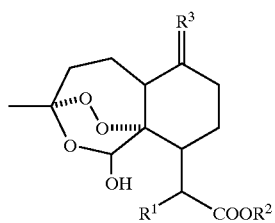
as an active component.
4. The therapeutic agent for malaria according to claim 3, wherein the compound represented by the general formula (I) is 12-hidroxy-2-(1-methoxycarbonylethyl)-5-oxo-10,11, 13-trioxatricyclo[7.2.0.0$^{1,6}$]tridecane represented by a following formula (II).
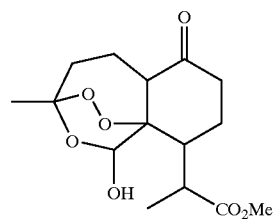
* * * * *